United States Patent
Beckers et al.

(10) Patent No.: US 9,506,880 B2
(45) Date of Patent: Nov. 29, 2016

(54) DIFFRACTION IMAGING

(71) Applicant: PANalytical B.V., Almelo (NL)

(72) Inventors: Detlef Beckers, Almelo (NL); Milen Gateshki, Almelo (NL)

(73) Assignee: PANALYTICAL B.V., Almelo (NL)

( * ) Notice: Subject to any disclaimer, the term of this patent is extended or adjusted under 35 U.S.C. 154(b) by 0 days.

(21) Appl. No.: 14/311,659

(22) Filed: Jun. 23, 2014

(65) Prior Publication Data

US 2015/0003592 A1 Jan. 1, 2015

(30) Foreign Application Priority Data

Jun. 26, 2013 (EP) ..................................... 13173816

(51) Int. Cl.
*G01N 23/207* (2006.01)
*G01N 23/205* (2006.01)
*G01N 23/20* (2006.01)

(52) U.S. Cl.
CPC ...... *G01N 23/205* (2013.01); *G01N 23/20008* (2013.01); *G01N 2223/40* (2013.01)

(58) Field of Classification Search
CPC ............... G01N 23/207; G01N 23/20; G01N 2223/604
See application file for complete search history.

(56) References Cited

U.S. PATENT DOCUMENTS

2011/0268251 A1* 11/2011 He ........................ G01N 23/207
378/71

FOREIGN PATENT DOCUMENTS

WO WO 2011/139473 11/2011

* cited by examiner

*Primary Examiner* — Hoon Song
(74) *Attorney, Agent, or Firm* — Leason Ellis LLP

(57) ABSTRACT

A method of imaging phases in an inhomogeneous polycrystalline sample having a plurality of crystallites of at least a first crystalline component includes illuminating an illuminated area extending across a surface of a sample with substantially monochromatic X-rays incident at a Bragg-Brentano parafocussing geometry at first angle $\theta_1$ to the surface of the sample. X-rays diffracted by the sample at a second angle $\theta_2$ pass through a pinhole. The diffraction angle $\theta_1+\theta_2$ fulfils a Bragg condition for the first crystalline component which is imaged by a detector to provide a two-dimensional image of the first crystalline component at the surface of the sample.

17 Claims, 4 Drawing Sheets

DIFFRACTION IMAGING

FIELD OF INVENTION

The invention relates to imaging of phases in samples by X-rays.

BACKGROUND ART

In some fields it is useful to image the phase distribution in polycrystalline samples with small crystals or crystallites of one or more materials.

One approach that has been used is to use X-ray fluorescence. Imaging detectors may be used to build up an image of X-ray fluorescence across a sample and hence image the location of particular elements or phases. However, this approach is not suitable in all cases and in particular X-ray fluorescence only distinguishes the elements not the specific crystal or crystal phase concerned.

SUMMARY OF INVENTION

According to a first aspect of the invention there is provided a method of preparing samples according to claim 1.

By imaging in a Bragg condition it is possible to image the location of a particular component phase in the sample.

The incident X-rays may be incident on the illuminated area from an incident beam focus and the pinhole arrangement may be located at the focussing distance of the reflected X-rays. For symmetric conditions ($\theta_1=\theta_2$) this is substantially the same distance from the illuminated area of the surface of the sample as the incident beam focus.

The beams are thus incident on the Illuminated area of the sample at slightly diverging angles from the incident beam focus and not highly collimated. The incident beam focus may be a tube focus of an X-ray source or alternatively a slit or point. Additional collimation by slits, masks, other X-ray optics or for example a Soller slit is possible.

Prior approaches to imaging a polycrystalline sample using X-rays have used X-ray fluorescence, not X-ray diffraction. However, the application of X-ray fluorescence is limited to fluorescent materials. Where X-ray diffraction has been used for imaging, it has been used to image defects in almost perfect single crystals. Such imaging uses either a highly collimated incident beam or a pinhole on the incident beam side to achieve the same effect as a collimated incident beam to visualise defects in crystals. In addition, it is typically performed with low incident beam angles to get a sufficiently large illuminated area on the sample.

In contrast, the present invention illuminates an extended area of the sample. Inevitably, this results in the incident beam angle and beam direction not being identical across the illuminated area.

The inventors have realised that because the diffraction angle is given by the sum of the incident beam and diffracted beam angles $\theta_1+\theta_2$ a single diffraction condition, i.e. Bragg peak, may be maintained across a region of a sample large enough to carry out imaging of that region when the pinhole arrangement is placed in the focussing position of the reflected beam. Small variations in $\theta_1$ or $\theta_2$ are either small enough to remain within the Bragg peak. Also, at one edge of the illuminated area of the sample where $\theta_1$ is higher than in the centre $\theta_2$ may be lower than in the centre allowing for some compensation—the diffraction angle $\theta_1+\theta_2$ means that the Bragg condition may be met to sufficient accuracy across the illuminated area.

A sharp image can be achieved using a small pinhole positioned in the focussing condition of the reflected X-rays. This is not required when a fluorescence signal is imaged. Such fluorescent radiation is almost homogeneously scattered and so the pinhole can be placed anywhere. Thus, an image can be obtained simply by placing the pinhole and detector perpendicular to the sample surface.

For XRD, on the other hand, there is a need to fulfil the Bragg conditions so $\theta_1+\theta_2$ must be correct for the specific phase under investigation and the pinhole should be on the focussing circle.

The method may be used to image multiple component phases by changing the diffraction angle $\theta_1+\theta_2$ to correspond to a second crystalline component.

The detector may be a two-dimensional detector. Alternatively, a one-dimensional detector or a point detector may be used if the detector can be moved to different locations and/or orientations to build up a two-dimensional image.

To minimise distortions, the two-dimensional detector may be oriented parallel to the sample surface. Note that this is not the usual orientation of a two-dimensional detector which is typically oriented perpendicular to the diffracted X-rays, not the sample surface, in conventional X-ray diffraction measurements.

The sample and the detector may be wobbled in parallel keeping the sample surface parallel to the detector during the method of imaging. This can improve particle statistics and hence improve the imaging.

Alternatively, the pinhole arrangement and the detector may be oriented such that $\theta_2$ is close to 90°, for example 80° to 100°, preferably 85° to 95°, to eliminate distortion of the image. In this case, the incident beam may be adjusted to adjust $\theta_1$ for example in the range 5° to 75°, to achieve the Bragg condition. To achieve diffraction angles $\theta_1+\theta_2$ in a suitable range it is also possible to choose the characteristic wavelength of the X-ray tube accordingly.

For convenience, other angles may also be used.

The method may further comprise passing the monochromatic X-rays incident on the sample through a mask on the incident side of the sample to define the illuminated area. To control axial divergence, the monochromatic X-rays may also be passed through a Soller slit.

The axial divergence of the first angle $\theta_1$ and the pinhole size may be selected such that the variation of the diffraction angle $\theta_1+\theta_2$ across the illuminated area of the sample is large enough so that the Bragg condition for the first crystalline component is fulfilled across the illuminated area of the sample surface.

However, the axial divergence of the first angle $\theta_1$ and the pinhole size may be selected such that the variation of the diffraction angle $\theta_1+\theta_2$ across the illuminated area of the sample is small enough so that the Bragg condition is not fulfilled for neighbouring Bragg peaks to the Bragg peak for the said Bragg condition for the first crystalline component anywhere across the illuminated area of the sample surface.

A short scan may be carried out, to vary the diffraction angle $\theta_1+\theta_2$ by varying $\theta_1$, $\theta_2$ or both. This can improve diffraction intensity at the edges of the sample and improve particle statistics.

Conveniently, the pinhole arrangement is an actual pinhole, which is simple. However, a combination of collimating devices such as may be present in a secondary monochromator, may be used instead in which case the resolution is determined by the "rocking curve width" of the crystal reflection in the monochromator.

BRIEF DESCRIPTION OF DRAWINGS

Embodiments of the invention will now be described, purely by way of example, with reference to the accompanying drawings, in which.

The figures are schematic and not to scale.

DETAILED DESCRIPTION

Figure 1:
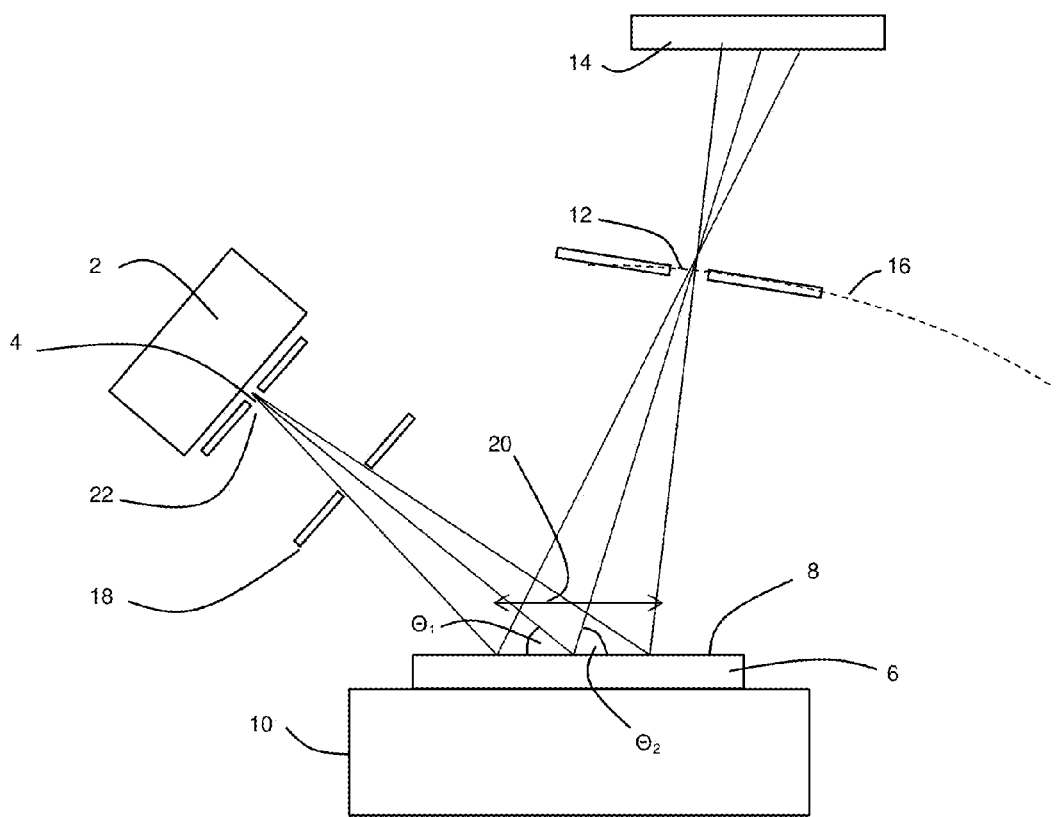
FIG. 1 shows a schematic drawing of an apparatus used in a method according to the invention.

Referring to FIG. 1, a highly schematic representation of the general set-up includes a tube 2 with tube focus 4, a pinhole 12 and a detector 14. A polycrystalline sample 6 with a sample surface 8 is mounted on sample mount 10.

X-rays emerge from the tube and are incident across an illuminated area 20 of the sample surface. The X-rays are diffracted there and are incident on the pinhole 12 which is at the distance that corresponds to the para-focussing conditions. This is represented by a focussing line in FIG. 1. For a symmetric reflection $\theta_1 = \theta_2$ the pinhole is substantially at the same distance from the sample as the tube focus.

The X-rays are incident at incident angle $\theta_1$ and diffracted at diffraction angle $\theta_2$ from the surface and pass through the pinhole 12 onto the detector 14 which in this embodiment is a two-dimensional detector that can directly image the sample surface 8.

The diffraction angle is $\theta_1 + \theta_2$. This diffraction angle is chosen to meet the Bragg condition for a particular component of the polycrystalline sample, i.e. a particular phase. Thus, only that component will be imaged.

The illumination X-rays are substantially monochromatic and a single line of the incident X-ray tube may be used.

Note that the condition that the pinhole 12 is at the same distance to the sample surface 8 as the tube focus 4 applies only to the symmetric condition $\theta_1 = \theta_2$.

Where this condition does not apply, the following equation (the Bragg-Brentano para-focussing geometry) applies:

$$t \sin \theta_2 = r \sin \theta_1$$

with t the distance of tube focus 4 to sample surface 8 and r the distance of pinhole 12 to sample surface 8.

In this case, the location of the pinhole is accordingly at a position determined by the Bragg-Brentano parafocus geometry, namely the position that the X-rays diffracted to have constant diffraction angle $\theta_1 + \theta_2$ pass through. For a given $\theta_1$, there is a position for each $\theta_2$ at a distance given by the equation above at which to first order the beams pass through a point. This position is the parafocal position. Of course, in a conventional Bragg-Brentano geometry a single detector (or entrance to a detector) is located at a location determined by the parafocal condition whereas in the present invention a pinhole arrangement is located at this point and used to provide a two-dimensional image of a surface of the sample on a detector located behind the pinhole arrangement.

Figure 2:
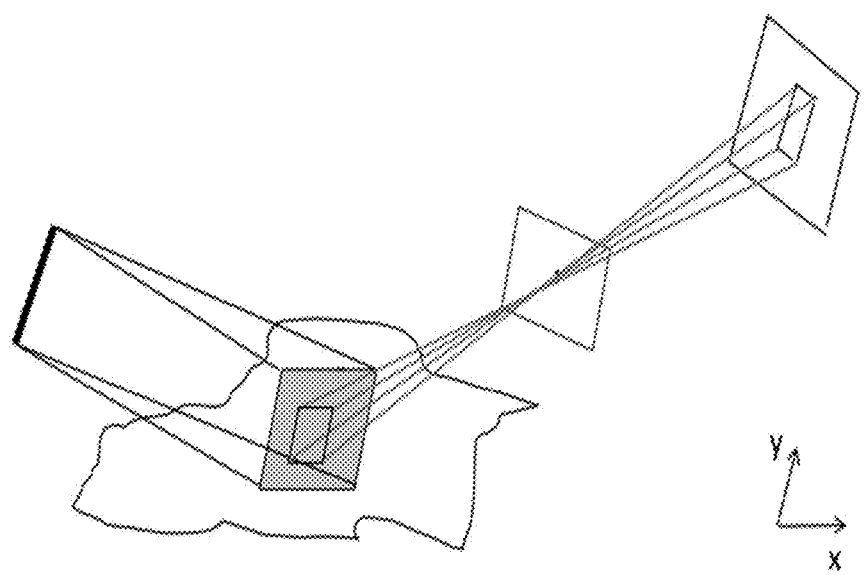
FIG. 2 shows a perspective view of the optical arrangement of the apparatus of FIG. 1 from a different direction.

FIG. 2 illustrates the geometry in perspective view.

A number of specific approaches can be used to illuminate the sample.

In a first approach, a tube 2 is used in a line focus arrangement with a large slit and a mask 18 which are used to determine the illuminated area 20 of the sample as illustrated in FIGS. 1 and 2.

An optional Soller slit 22 may be provided on the incident beam side, between the focus position 4 and the sample 8. This Soller slit is used to control the beam divergence at the sample surface 8, by limiting the angles of X-rays from the focus position 4.

Note that the pinhole position determines the peak position and the size of the pinhole determines whether only one peak or multiple peaks go through, that is to say a smaller pinhole gives better resolution. The axial divergence of the X-rays, which may be controlled by the Soller slit, together with the peak width, determine how well the edges of the sample can be imaged.

The Bragg diffraction peak selected for imaging should not overlap with peaks of other phases.

In an alternative approach a point focus with an aperture in front of the tube may be used.

Images obtained using this apparatus and method are presented in FIGS. 3 to 6.

Figure 3:
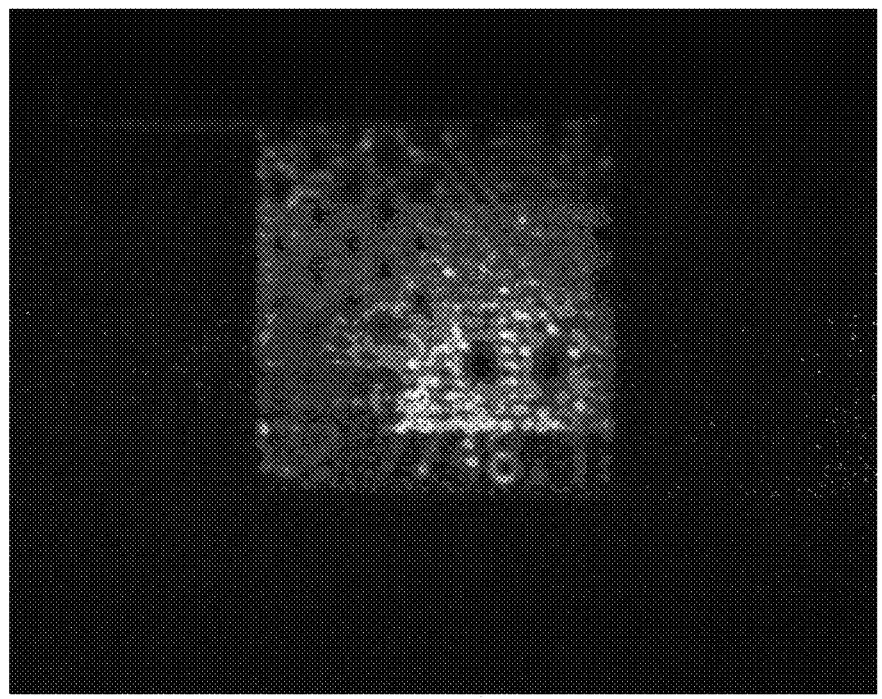
FIGS. 3 to 6 show images of various samples recorded using the method of an embodiment of the invention.
Figure 4:
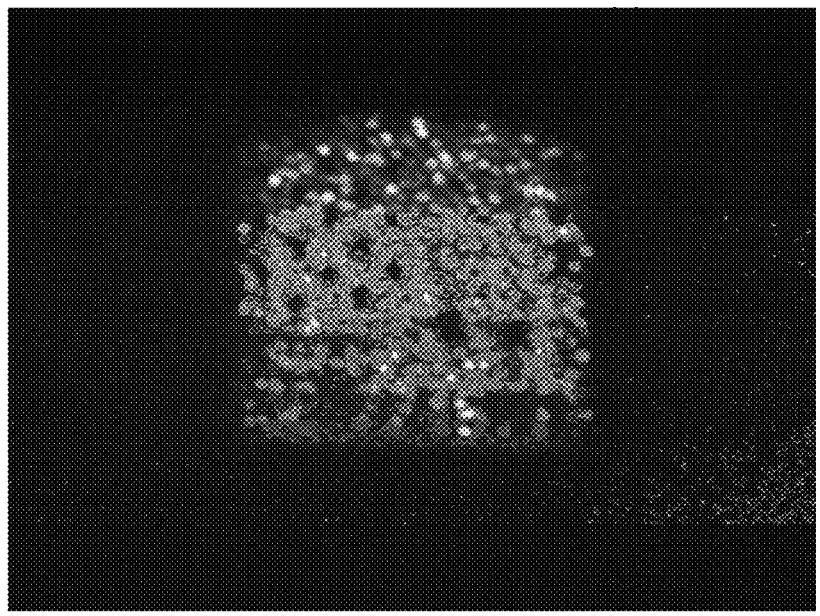

FIG. 3 is an image of a printed circuit board made using a line focus and FIG. 4 an image of the same board using a point focus. Note in this case the line focus gives better imaging.

Figure 5:
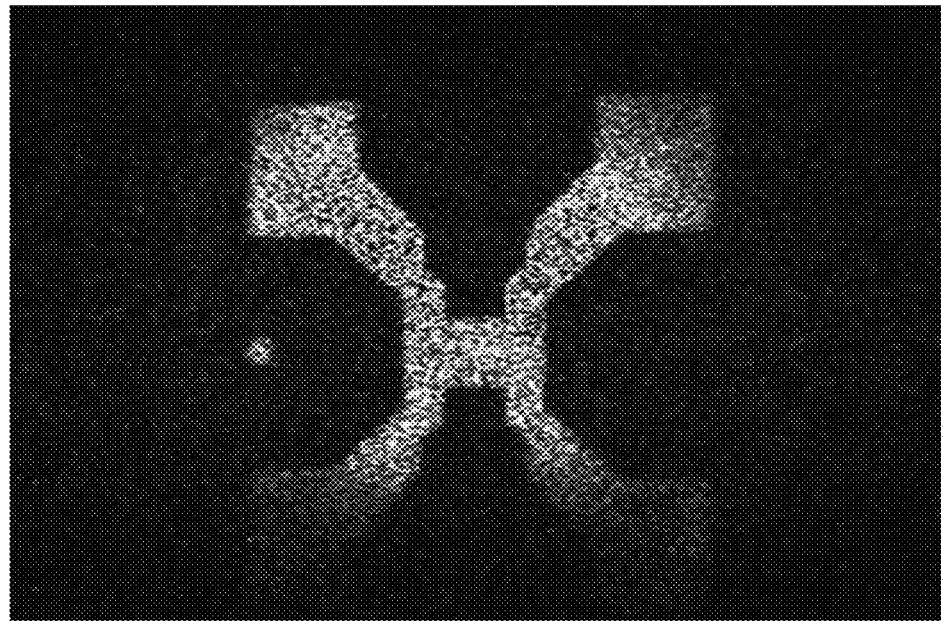

FIG. 5 is an image of a gold layer on silicon (the pads of a silicon chip).

Figure 6:
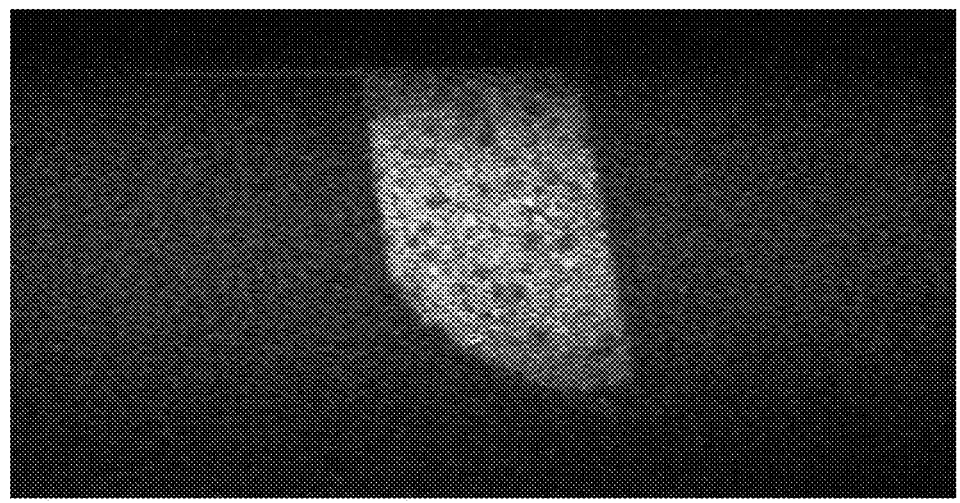

FIG. 6 is an image of a meteorite section imaged using a line focus. Note that in this case the material is fluorescent and so an overlying XRF signal is also seen.

Note that good imaging of the location of individual crystallites may be seen.

For normal diffraction imaging the detector surface is perpendicular to the radial direction. However, to minimise imaging distortion it is preferred that the detector surface (the imaging plane of detector 14) is parallel to the plane of the sample surface 8.

In the case that the imaging plane of detector 14 is not parallel to the plane of the sample surface 8 then geometric correction may be applied by projecting the image captured by the detector onto a plane parallel to the sample surface. Such projection may be carried out in software.

To improve particle statistics in this specific case the sample surface 8 and the detector surface may be wobbled in parallel, i.e. the angle of orientation of sample remains parallel to the detector surface as both are varied.

The pinhole size may be selected to match the achievable resolution of the detector bearing in mind the need for sufficient X-rays to image in a reasonable length of time. The achievable spatial resolution at the sample surface depends on the pinhole size, pixel size of the detector, orientation of the detector relative to the surface, the angle $\theta_2$ and the axial divergence of the beam.

A scan in $\theta_1$, $\theta_2$ or both (over a short range) may be carried out to improve the diffraction intensity from the edge of the sample by accumulation of images and to improve particle statistics.

The invention allows the measurement of the location of different crystal phases across the sample surface.

The magnification of the image can be very easily changed simply by changing the distance of the detector to the pinhole.

The size of the pinhole may be adjusted to achieve a trade-off between spatial resolution and image intensity. A large pinhole passes more X-rays, achieving a higher image intensity and hence lower measurement time, but achieves a lower spatial resolution.

No dedicated microspot optics are required and the components used such as a pinhole and a line source focus are readily available. Further, sample motion is not required. The incident beam does not need to be highly collimated and no monochromator is required—the line width of an X-ray source line is normally sufficient. For these reasons, the method allows imaging without the expense of very high quality equipment.

Multiple images may be obtained, each image of a different phase. If required, these can be combined by image processing.

Note that the approach does require relatively small crystallites to achieve a sufficient probability for reflection at the diffraction angle through the pinhole. This effect can be reduced by scanning or wobbling to improve statistics, for example as discussed above.

However, if the sample contains larger crystallites with a certain preferred orientation that allow beam reflection through the pinhole, imaging of that particular phase (at constant $\theta_1+\theta_2$) with different incident beam angles $\theta_1$ allows to investigate the orientation of these crystallites in the sample surface (crystallite orientation imaging).

In an alternative embodiment, 1 D detectors can be used with a receiving slit and the second dimension can be built up by sample rotation.

Another alternative is to keep the use of a pinhole and to rotate a 1 D detector to build up an image, The pinhole 12 may be replaced by other combinations of collimating optics such as a secondary monochromator with a slit and the spatial resolution in this case is determined by the slit size and rocking curve width of the crystal reflection. In this case, the pinhole arrangement is not a true pinhole but something with the same effect, i.e. an entry window of limited size.

In order to identify suitable diffraction angles $\theta_1+\theta_2$ the apparatus can first be used using the detector as a point detector i.e. without obtaining an image to identify diffraction angles that give rise to a useful signal. A two-dimensional image may then be obtained using a method as set out above for the diffraction angle or angles that are identified.

The invention claimed is:

1. A method of imaging an inhomogeneous polycrystalline sample having a plurality of crystallites of at least a first crystalline component, comprising:
   illuminating an illuminated area extending across a surface of a sample with substantially monochromatic X-rays from an incident beam focus, the substantially monochromatic X-rays being incident at a first angle $\theta_1$ to the surface of the sample; and
   passing X-rays diffracted by the sample at a second angle $\theta_2$ through a pinhole arrangement, wherein the diffraction angle $\theta_1+\theta_2$ fulfils a Bragg condition for the first crystalline component, and the pinhole arrangement is located at a position determined by a parafocus condition, the X-rays passing through the pinhole arrangement and onto a detector spaced from the pinhole arrangement, wherein the pinhole arrangement provides a two-dimensional image of the first crystalline component at a surface of the sample on the detector.

2. The method according to claim 1, wherein the incident X-rays are incident on the illuminated area from an incident beam focus and wherein the pinhole arrangement is located at substantially the same distance from the illuminated area of the surface of the sample as the incident beam focus.

3. The method according to claim 1 further comprising changing the diffraction angle $\theta_1+\theta_2$ to correspond to a second crystalline component of the inhomogeneous polycrystalline sample to provide a two-dimensional image of the second crystalline component at the surface of the sample.

4. The method according to claim 1 wherein the detector is a two-dimensional detector.

5. The method according to claim 4 wherein the two-dimensional detector is oriented parallel to the sample surface.

6. The method according to claim 5 wherein the sample and the detector are wobbled in parallel keeping the sample surface parallel to the detector during imaging.

7. The method according to claim 1 wherein the pinhole and the detector are oriented such that $\theta_2$ is 80° to 100°, preferably 85° to 95°.

8. The method according to claim 1 wherein $\theta_1$ is in the range 5° to 70°.

9. The method according to claim 1 further comprising passing the monochromatic X-rays incident on the sample through a hole or slit in a mask on the incident side of the sample to define the illuminated area.

10. The method according to claim 1 further comprising passing the monochromatic X-rays through a Soller slit to control the axial divergence of the first angle $\theta_1$ across the illuminated area.

11. The method according to claim 10 wherein the axial divergence of the first angle $\theta1$ and the pinhole arrangement are selected such that the variation of the diffraction angle $\theta1+\theta2$ across the illuminated area of the sample is small enough so that the Bragg condition is not fulfilled for neighbouring Bragg peaks to the Bragg peak for the said Bragg condition for the first crystalline component anywhere across the illuminated area of the sample surface.

12. The method according to claim 1 further comprising illuminating the sample with a multilayer, alpha-1 monochromator or X-ray lens.

13. The method according to claim 1 wherein the axial divergence of the first angle $\theta_1$ and the pinhole arrangement are selected such that the variation of the diffraction angle $\theta_1+\theta_2$ across the illuminated area of the sample is large enough so that the Bragg condition for the first crystalline component is fulfilled across the illuminated area of the sample surface.

14. The method according to claim 1 further comprising varying the diffraction angle $\theta_1+\theta_2$ by varying $\theta_1$, $\theta_2$ or both.

15. The method according to claim 1 further comprising adjusting the size of the pinhole arrangement to select spatial resolution and intensity passing through the slit.

16. The method according to claim 1 comprising performing several imaging steps for the same Bragg reflection $\theta_1+\theta_2$, with different incident beam angles $\theta_1$ to investigate the orientation of the crystallites of a certain phase in the sample surface.

17. A method comprising
   illuminating the sample with X-rays;
   using the detector as a point detector to detect at least one suitable diffraction angle $\theta_1+\theta_2$;
   illuminating an illuminated area extending across a surface of a sample with substantially monochromatic X-rays from an incident beam focus, the substantially monochromatic X-rays being incident at a first angle $\theta_1$ to the surface of the sample; and
   passing X-rays diffracted by the sample at a second angle $\theta_2$ through a pinhole arrangement, wherein the diffraction angle $\theta_1+\theta_2$ fulfils a Bragg condition for the first crystalline component, and the pinhole arrangement is located at a position determined by a parafocus condition, the X-rays passing through the pinhole arrangement and onto a detector spaced from the pinhole arrangement, wherein the pinhole arrangement provides a two-dimensional image of the first crystalline component at a surface of the sample on the detector.

* * * * *